US00PP10623P

United States Patent [19]

Wouters

[11] Patent Number: Plant 10,623

[45] Date of Patent: Sep. 29, 1998

[54] VARIETY OF APPLE TREE BEL-EL

[75] Inventor: Kris Wouters, Rummen, Belgium

[73] Assignee: Jomobel NV, Belgium

[21] Appl. No.: 783,405

[22] Filed: Jan. 13, 1997

[51] Int. Cl.[6] ..... A01H 5/00

[52] U.S. Cl. ..... Plt./34.1

[58] Field of Search ..... Plt./34.1

[56] References Cited

U.S. PATENT DOCUMENTS

P.P. 6,450 12/1988 Visser ..... Plt./34.1

OTHER PUBLICATIONS

GTITM UPOV–ROM Plant Variety Database citation for 'Bel–El' DE PBR APF 00052, proposed Jun. 18, 1990, published Oct. 15, 1990.

*Primary Examiner*—James R. Feyrer

*Attorney, Agent, or Firm*—Olson & Olson

[57] ABSTRACT

A new and distinctive variety of apple tree named Bel-El, a sport mutation of the apple variety Elstar, uniquely characterized from its parent variety by the tree's distinctly-colored branches and the distinctly-colored petioles and nerves in its leaves, and by its less dense, bushy foliage than its parent variety, its fruit further characterizing the new variety from its parent by its solid red color, its longer, thinner brown/red stalk, and by its earlier ripening and picking dates.

4 Drawing Sheets

BACKGROUND OF THE INVENTION

This invention relates to a new and distinct variety of apple tree (*Malus domestica*), named Bel-El.

The new apple variety was discovered in a cultivated Elstar apple orchard located at Rummen, Belgium as a sport mutation of the Elstar apple tree, U.S. Plant Pat. No. 6,450. It was noted that five of the trees in the orchard were unique and different in appearance from the entire block of Elstar trees in that they were bearing dark red apples in about mid-August while the rest of the Elstar orchard fruit was still green. These trees were propagated with the buds taken from one spontaneous mutated branch.

Observation of the five trees made from the mutated branch over a period of three weeks indicated that the condition of the fruit remained stable although its color gradually became blood red. Extended observation in Halen, Belgium has shown that the unique and distinguishing characteristics of the descendants from the new mutation and their fruit have remained consistent through their third generation descendants.

The major differences between the parent Elstar apple variety and the new Bel-El apple variety are itemized in the following comparision table.

TABLE A

| | ELSTAR | BEL-EL |
|---|---|---|
| TREE | | |
| vigour | strong | medium-strong |
| figure | medium to large | medium |
| density | dense | less dense |
| color of branches | green-brown | has a red-brown upper side and a green-brown lower side |
| predominance of bearing | on spurs | on spurs |
| LEAF BLADE | | |
| leaf; petiole + nerves | upper side: green lower side: rose/red | upper side: green lower side: darker purple/red |
| FLOWER | | |
| color of flower | red-purple(58/A) | greyed-purple (187/D+C) |

TABLE A-continued

| | ELSTAR | BEL-EL |
|---|---|---|
| color of full bloom | red-purple(71/A+D) | greyed-purple (186/C+A) |
| FRUIT | | |
| color intensity of the ripe fruit | yellow/green with bright-red slightly spotted-striped blush | a dark-red solid flush over practically 100% of the surface of the skin |
| size | medium-large | medium-large larger than Elstar |
| axial diameter | 2-½ inch at 3-⅛ inch; mean = 2-¾ inch | 2-¾ inch at 3-¼ inch; mean = 3 inch |
| transverse diameter | 2-¼ inch to 2-½ inch; mean = 2-⅜ | 2-½ inch at 2-¾ inch; mean = 2-½ inch |
| shape | globose-conical conic to slightly oblong, broad, rounded at base, side usually slightly unequal | global-conical |
| prominence of ribbing | weak | very weak |
| aperture of eye | half open (some closed) | mainly closed (some half open) |
| stalk | shorter, thicker, brown/green | about 0.5 cm longer, thinner, red/brown |
| begin of coloring | end of August | keeps its red color from the stage when the apple is small. The difference can be noticed over the whole period. At the end of August, the apple is already red. |
| amount of over color of skin | medium | high-very high |
| over color of skin | red | darker red |
| type of over color of skin | mottled(with area) of solid flush) | solid flush; approx. 20% of the fruit show some spots, mottles or stripes. |
| time of picking | between 15 and 30 September | between 30 August and 15 September. |

TABLE A-continued

| | ELSTAR | BEL-EL |
|---|---|---|
| sugar level | | sweeter, earlier |
| FRUIT RIPENING | | |
| time of fruit ripening for eating | late | medium |

THE DRAWINGS

DESCRIPTION OF THE NEW VARIETY

Figure 1:
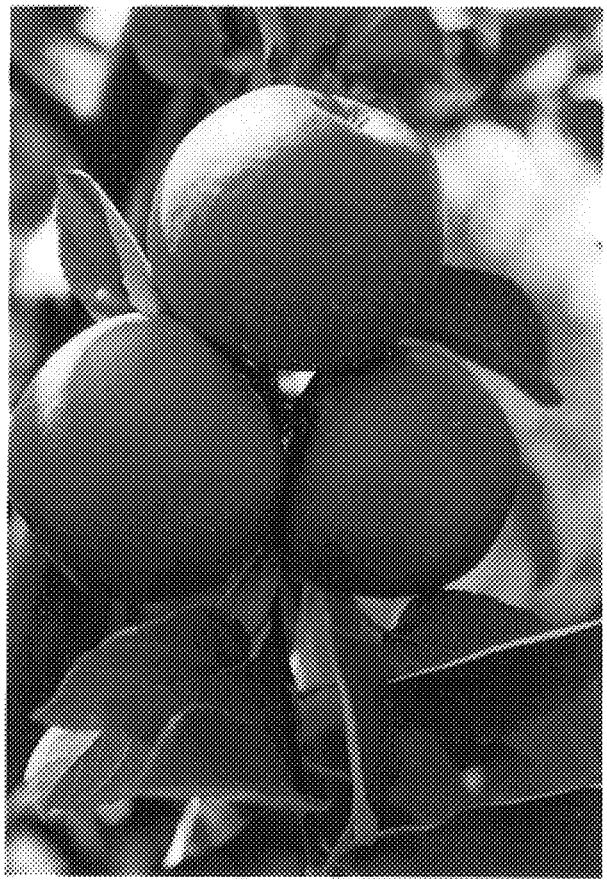
FIG. 1 is a close-up view showing the color and appearance of the fruit and leaves on a branch of the new apple variety Bel-El.
Figure 2:
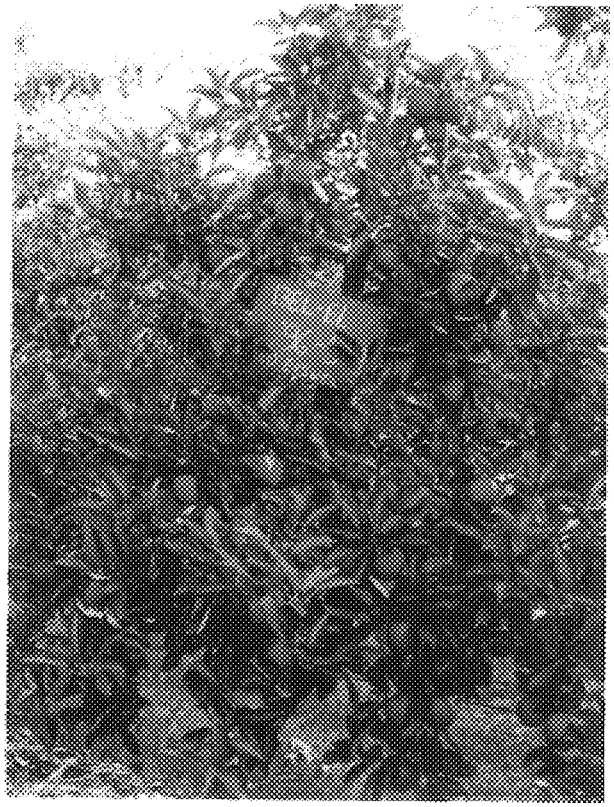
FIG. 2 illustrates the overall appearance and growth habit of the Bel El apple tree.
Figure 3:
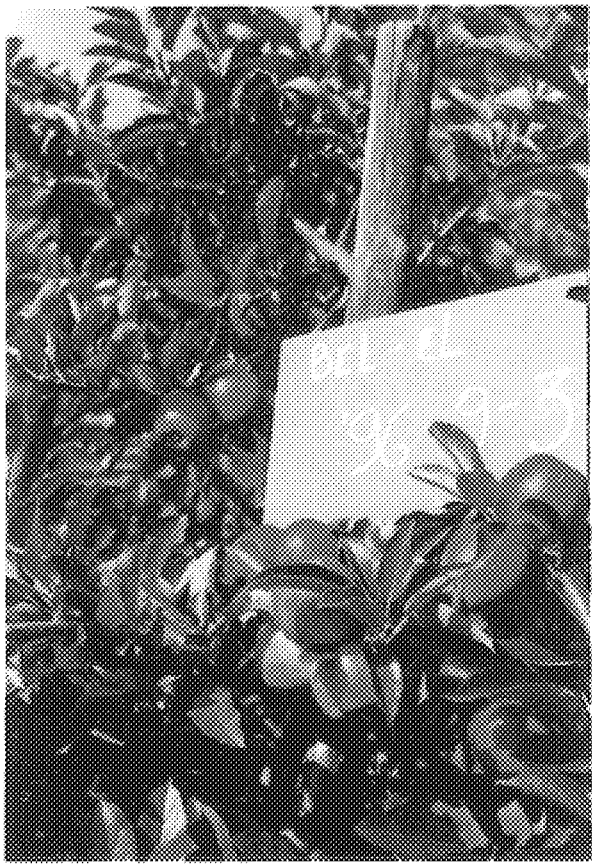
FIG. 3 is a closer view of a portion of the Bel-El apple tree shown in FIG. 2 showing the presence of some mottles, stripes or spots on approximately 20% of the fruit.
Figure 4:
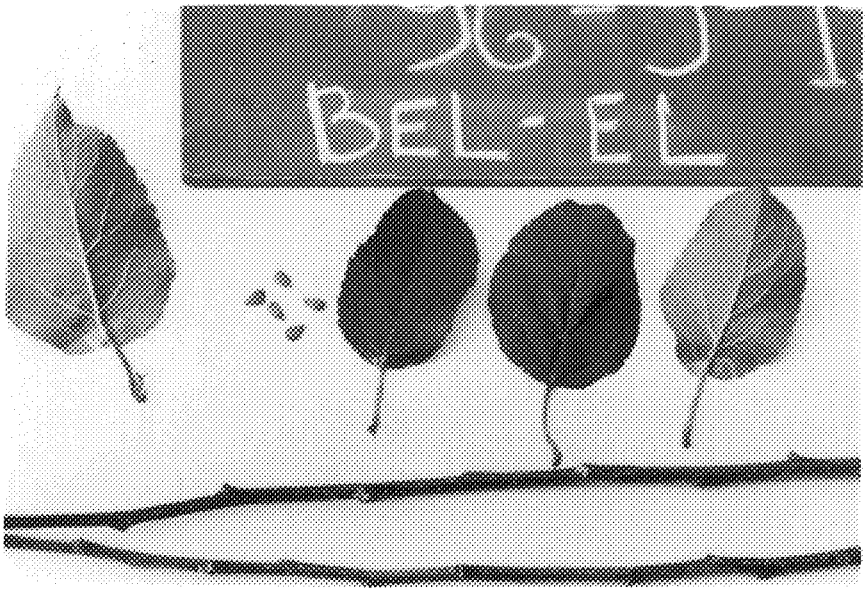
FIG. 4 is a view of the leaves and branches of the new apple tree, along with the seeds of its fruit.
Figure 5:
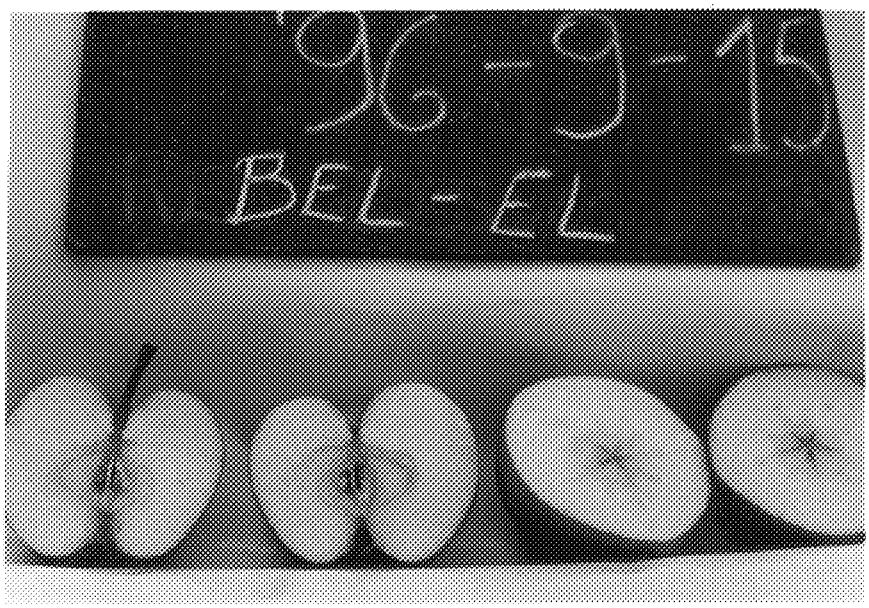
FIG. 5 is a view illustrating longitudinal and transverse sections taken through the fruit of the Bel-El apple variety.

The following is a detailed description of the new apple tree variety Bel-El as grown and observed in Halen, Belgium. Color references are made to The Royal Horticultural Colour Chart of London in association with the Flower Council of Holland-Leiden (1986), except where general color terms of ordinary dictionary significance are used.

Parentage: A sport mutation of the apple tree variety Elstar.
Propagation: Asexually by budding and grafting.

The Tree

Form: Medium size, slightly bushy and dense foliage.
Habit of growth: Generally rapid, very productive.
Vigor (based on height and spread): Medium strong.
Trunk: Medium stocky, smooth, medium strong.
Branches: Much branching, upright spreading.
Density of Head: Dense.
Predominance of bearing: On spurs.
Dormant one-year-old shoot: Medium thick, medium pubescence (on upper half of shoot) with a medium number of lenticels, a red-brown upper side and a green-brown underside.
Leaves:
(1) *General pose.*—Upward and outward.
(2) *Size.*—Large; oval; length—from 8.6 to 12. 4 cm., width—from 4.5 to 6.01 cm.
(3) *Petiole.*—Long; from 3.01 to 4.04 cm.
(4) *Leaf blade.*—Strong glossiness of upper side and a medium pubescence on underside. Dark green color.
(5) *Margin.*—Crenate, bicrenate, serrate and biserrate. During the ripening time of the fruit, the veins on the underside of the leaves are greyed-purple (group 185B).
Flowers:
(1) *Time of begining of flowering.*—Late.
(2) *Finishing date of flower.*—Approximately 12 May.
(3) *Size.*—Medium diameter flower with petals pressed into horizontal position.
(4) *Color of flower bud.*—Greyed-purple (187/D+C).
(5) *Color in full bloom.*—Greyed-purple (186/C+B).
(6) *Color at end of bloom.*—Greyed-purple (186/C+A).

The Fruit

Fruit:
*Dates of first and last picking.*—Approximately 30 August and 15 September, respectively.
*Time of fruit ripening for eating.*—Medium.
*Maturity when described.*—Ripe for eating.
*Size.*—Medium to large fruit.
*Form.*—Global—conical. Vertical diameter of approximately 6.56 cm, horizontal diameter of approximately 7.71 cm.
*Symmetry in side view* (*predominant situation*).—Asymmetric.
*Ribbing.*—Present. Prominence of ribbing-very weak.
*Crowning at distal end.*—Present. Degree: weak.
*Aperture of eye.*—Mainly closed, some half open.
*Size of eye.*—Medium.
*Length of sepal* (*visual*).—Long. Spacing of sepals at base: touching.
*Depth of eye basin.*—Medium. Width of eye basin: medium.
*Stalk.*—Color: brown/red. Thickness: medium-thick, approximately 3.15 mm. Length: Long, approximately 3.55 cm. Depth of stalk cavity: deep.
*Width of stalk cavity.*—Medium-broad.
*Skin.*—Relief of surface: bumpy, slightly rough.
*Bloom of skin.*—Absent.
*Greasiness of skin.*—Present. Cracking tendency of skin: absent.
*Thickness of skin.*—Medium. The skin finish: less shiny.
*Ground color of skin.*—Yellow group 10.A.
*Over color of skin.*—Red; darkest red (red group 46.A) and lightest red (red group 46.B). Amount of over color: high-very high. Type: solid flush. Approximately 20% of fruit exhibits some mottles, spots or stripes.
*Lenticels.*—Size: medium.
*Amount of russet.*—Low. Position of russet: around stalk cavity.
*Flesh.*—Browning of the flesh(one hour after being cut, with stainless steel knife): absent or very weak. Firmness of the flesh: medium/firm. (measurement with penetrometer: 6.53). Color of the flesh: Cream; yellow group 13D. Texture of the flesh: medium. Juiciness: juicy.
*Seeds.*—Length: 0.9 cm. Breadth: 0.5 cm. Form: acute. Color: brown (Greyed orange group. 165A).
*Fruit in cross-section.*—Distinctness of core-line (median through locules): medium. Aperture of locules: closed.
*Tree-storing capacity.*—Fruit remains in good condition on tree for approximately one month or so beyond picking date, with no apparent formation of water core when so stored.
Other characteristics:
*Use.*—Particularly well-suited as a dessert fruit; juices.
*Keeping quality.*—Natural conditions: Good; refrigerated conditions: Keeps very well up to seven months.

*Resistance to insects and diseases.*—No unusual susceptibility or resistance noted.

I claim:

1. The new and distinct variety of apple tree named Bel-El as described and illustrated, and which is particularly characterized over its parent variety by the red solid flush and longer, thinner brown/red stalk of its fruit; by the earlier picking dates of its fruit; by the tree's distinctly-colored branches which have a red/brown upper side and a green/brown underside and leaves in which the petioles and nerves are green on the upper side and dark purple/red on the underside; and by its less dense, bushy foliage than its parent variety.

* * * * *